(12) United States Patent
Liu et al.

(10) Patent No.: US 7,847,025 B2
(45) Date of Patent: Dec. 7, 2010

(54) AMPHIPHILIC BLOCK COPOLYMERS AND THEIR USE

(75) Inventors: Yan Liu, Hässleholm (SE); Jöns Gunnar Hilborn, Sigtuna (SE); Hendrick Jan Haitjema, Peize (NL); Sverker Norrby, Leek (NL); Thom Terwee, Roden (NL)

(73) Assignee: AMO Groningen B.V., Groningen (NL)

( * ) Notice: Subject to any disclaimer, the term of this patent is extended or adjusted under 35 U.S.C. 154(b) by 1343 days.

(21) Appl. No.: 11/314,930

(22) Filed: Dec. 20, 2005

(65) Prior Publication Data

US 2006/0134177 A1    Jun. 22, 2006

Related U.S. Application Data

(60) Provisional application No. 60/638,051, filed on Dec. 20, 2004.

(30) Foreign Application Priority Data

Dec. 20, 2004    (SE) ................................... 0403092

(51) Int. Cl.
*C08L 83/08*    (2006.01)

(52) U.S. Cl. .................. 525/100; 424/427; 514/63; 556/400; 623/6.56; 623/4.1; 623/926

(58) Field of Classification Search ................ 525/100; 424/427; 623/6.56, 4.1, 926; 514/63; 556/400
See application file for complete search history.

(56) References Cited

U.S. PATENT DOCUMENTS

| 4,740,533 | A | * | 4/1988 | Su et al. ..................... 523/106 |
| 5,739,192 | A | * | 4/1998 | Blizzard et al. ............. 524/379 |
| 5,807,944 | A | * | 9/1998 | Hirt et al. ................... 526/279 |
| 5,993,972 | A | * | 11/1999 | Reich et al. ............... 428/423.1 |

FOREIGN PATENT DOCUMENTS

| EP | 0 395 583 A2 | 10/1990 |
| EP | 1 364 663 A1 | 11/2003 |
| WO | WO 99/12059 | 3/1999 |
| WO | WO 01/76651 | 10/2001 |

* cited by examiner

*Primary Examiner*—Ling-Siu Choi
*Assistant Examiner*—Chun-Cheng Wang

(57) ABSTRACT

The present invention relates to amphiphilic block copolymers comprising at least one block of hydrophilic units and at least one block of hydrophobic units, wherein at least one hydrophobic block contains siloxane units. The present invention may be particularly useful as a tissue adhesive or as a coating for an intraocular lens (IOL). As an IOL coating, copolymers according to the invention may be used, for example, to promote tissue adhesion for the prevention of posterior capsule opacification.

20 Claims, 3 Drawing Sheets

¹H-NMR bisisothiocyanate-terminated poly(dimethyl-co-phenyl-co-trifluoropropylmethylsiloxane)-b-poly(ethylene glycol) (*III*)

ESCA spectrum of the collagen film without coating

ESCA spectrum of collagen film coated with the copolymer in method Ex 7B.

AMPHIPHILIC BLOCK COPOLYMERS AND THEIR USE

RELATED APPLICATIONS

This application claims priority under 35 U.S.C. §119 of U.S. Application Ser. No. 60/638,051 filed Dec. 20, 2004, and of Swedish Patent Application No. 0403092-0, filed on Dec. 20, 2004, both of which are incorporated by reference in their entirety herein.

TECHNICAL FIELD OF THE INVENTION

The present invention relates to amphiphilic block copolymers and to compositions comprising said copolymers. Furthermore, the present invention relates to the use of such compositions especially for modifying tissue surfaces and preventing secondary cataract.

BACKGROUND OF THE INVENTION

In many applications in the body involving implants, it is often desirable to create some type of connection between a tissue (a tissue is defined as any part of the body) and the implant (an implant is herein defined as anything which could be implanted into the body, e.g. a breast implant, a intraocular lens or a drug delivery device). The most common way to create such a connection is to use some type of adhesive. The adhesives used in general are cyanoacrylates and fibrin glues. Cyanoacrylates (disclosed in e.g. U.S. Pat. No. 6,183,593 and EP 0925795) have the advantage of fast bonding speed and strong bonds. However, they are also known to be toxic to some tissues and their potential degradation products are suspected to be carcinogenic. Further, the strong bonds formed can be a disadvantage in applications where flexible bonds are required. The fibrin glues (disclosed in e.g. U.S. Pat. No. 6,699,484 and U.S. Pat. No. 6,596,318) have the advantage of being degradable and non-toxic. However, the disadvantage with using fibrin glue is that tissue binding with fibrin glue cannot be subjected to even moderate tensile strength without rupturing the bond. Further, there is a risk of viral infection since fibrin glue is often of animal origin.

Another type of adhesive composition is provided by WO 02/087642, in which a water-absorbent two-phase adhesive composition containing a hydrophobic phase and a hydrophilic phase is disclosed. The hydrophobic phase is composed of a crosslinked hydrophobic polymer composition and the hydrophilic phase is a water-absorbent blend of a hydrophilic polymer and a complementary oligomer capable of crosslinking the hydrophilic polymer through hydrogen bonding, ionic bonding, and/or covalent bonding. The composition is useful as a bioadhesive, for affixing drug delivery systems, wound dressings, bandages, cushions, or the like to a body surface such as skin or mucosal tissue.

International Patent Application WO 03/097759 discloses biomedical adhesives comprising multi-functionally activated groups. The adhesives are used for bonding an implant to a surface, which surface can be either electrophilic or nucleophilic as long as it is opposite to the functional groups of the adhesive. The adhesive is coated on the implant.

There is, however, still a need for a biocompatible composition comprising compounds that will easily provide a coating on the tissue surface, which will facilitate the connection between said surface and an implant, and that will create a safe and flexible connection between said surface and the implant.

Cataract extraction is among the most commonly performed operations in the world. In this operation the natural lens is removed and replaced with an artificial intraocular lens (IOL), which will mimic the transparency and the refractive function of a natural lens. The intraocular lens can either be implanted into the capsular bag or injected as an ophthalmic composition into the capsular bag and then crosslinked (the capsular bag is used as a mold). The removal of the natural lens can be performed by several known techniques, e.g. phacoemulsification, which technique entails the application of ultrasonic energy or other forms of energy to the natural lens, thus breaking the lens into fragments that can be aspirated from the capsular bag.

Lens removal with an artificial lens implantation provides significant benefits to most cataract patients (currently lens removal with artificial lens implantation is increasingly carried out in a non-catarcatous eye, so-called refractive lens exchange, often with the purpose to relieve presbyopia). However, it is estimated that up to fifty percent of all patients, who have implants placed within the capsular bag, will develop capsular opacification (CO), also known as secondary cataract or "after cataract", within five years after surgery. CO is an opacification located on the inner surface of capsular bag, whether located posteriorly (PCO) or anteriorly (ACO) and is caused by deposition (the cell may be deposited on the interior surface of the capsular bag or on the implanted lens) or ingrowths of cells, cell derivatives and/or fibers into the visual axis and/or extracellular matrix production by the lens epithelial cells. The problem with CO is that the optical axis of the eye will be occluded, which will cloud the vision. Ophthalmic surgeons take considerable care in trying to remove as many as possible of the lens epithelial cells prior to implantation or injection of an artificial lens. However, despite these efforts, a significant number of lens epithelial cells are usually left on the interior surface of the capsular bag since these cells are difficult to view and often difficult to reach and virtually impossible to completely remove.

The most common treatment for postoperative PCO uses laser energy, however, the laser energy applied to the posterior membrane of the capsular bag is ordinarily directed though the implant and might damage the optic of said implant. Accordingly, it is desirable to prevent the occurrence of CO rather than treating CO. Various procedures for the prevention of CO have been suggested in recent years and a lot of those procedures have included the application of chemicals into of the capsular bag in order to destroy residual lens epithelial cells, e.g. WO 02/47728 that discloses a treatment of posterior capsular opacification by using a product comprising death receptor ligand covalently bound to a polymer. However, few if any of these procedures have proven to be particularly successful in the prevention of CO due to the fact that it is extremely difficult to destroy residual lens epithelial cells without simultaneously destroying other cells within the eye.

Another method for preventing secondary cataract is disclosed in the granted U.S. Pat. No. 6,702,853. This granted patent discloses a system and a method for preventing capsular opacification by applying an adhesive to at least one surface of implanted lens.

Thus, there is still a need for a method for preventing secondary cataract for system using injectable lenses, which method will affect the tissues and the optical properties of the injectable lens as little as possible.

BRIEF SUMMARY OF THE INVENTION

One object of the present invention is to provide amphiphilic block copolymers comprising at least one block of hydrophobic units and at least one block of hydrophilic units wherein the at least one block of hydrophobic units contains siloxane units.

Other objects of the present invention are to provide compositions comprising amphiphilic block copolymers and their use in applications such as tissue surface coating (i.e. modifying the tissue surface), providing a connection between an implant and a tissue surface and thereby preventing secondary cataract (capsular opacification).

Further objects according to the resent invention are to provide joined structures comprising amphiphilic block copolymers and their use.

Yet another object of the present invention is to provide a method for preventing secondary cataract, i.e. capsular opacification.

BRIEF DESCRIPTION OF THE DRAWINGS

The following detailed description will be more fully understood in view of the drawings in which FIGS. 1A and 1B set forth $^1$H-MNR spectra of an example.

DETAILED DESCRIPTION OF THE INVENTION

Figure 1A:
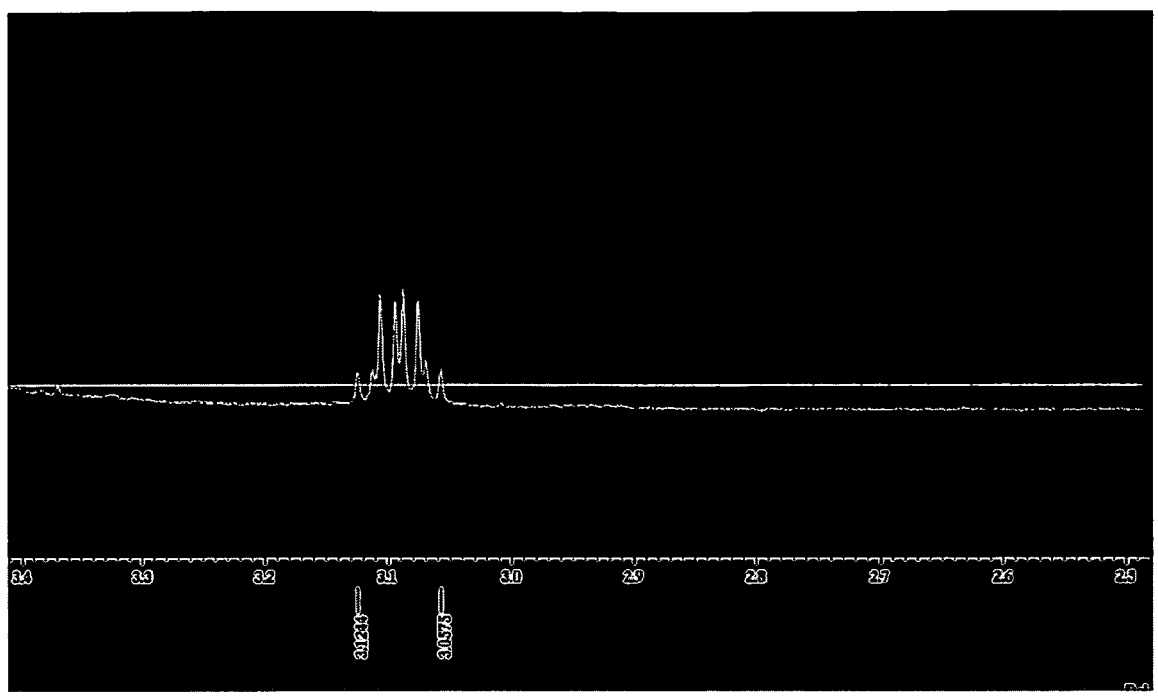

One aspect of the present invention is to provide an amphiphilic block copolymer, i.e. a polymer having blocks of two different monomers that appear together in the backbone e.g. A-A-A-B-B-B-A-A-A, comprising at least one block of hydrophilic units and at least one block of hydrophobic units wherein the at least one hydrophobic block contains siloxane units, i.e. SiO. The advantage of using amphiphilic copolymers in different applications is that said polymers are able to interact with two different phases (a hydrophobic phase and a hydrophilic phase) at the same time, thus an interaction between two otherwise incompatible phases is possible.

According to one embodiment of the present invention, the at least one block of hydrophobic units of the amphiphilic block copolymer comprises siloxane units having various optical properties. Said siloxane units comprise a copolymer, preferably a random terpolymer, having the formula:

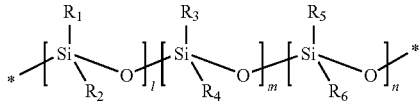

in which $R_1$, $R_2$, $R_3$ and $R_4$ are independently $C_1$-$C_6$ alkyl or aryl, $R_5$ and $R_6$ are independently fluoroalkyl or $C_{1-6}$ alkyl and l is in the molar fraction range of 0 to 0.95; m is in molar fraction range of 0 to 0.7; and n is in the molar fraction range of 0 to 0.65, most preferred is that $R_1$, $R_2$ and $R_6$ are methyl, $R_3$ and $R_4$ are phenyl and $R_5$ is trifluoropropyl. It is also preferred that said terpolymer has terminal amino groups. The hydrophobic block/blocks should preferably comprise essentially the same hydrophobic polymer as the implant since this will give the hydrophobic interaction between said block copolymer and the implant.

Another embodiment according to the present invention is that at least one block of hydrophilic units comprises a hydrophilic polymer selected from a biocompatible polymer which can easily form a block copolymer with the hydrophobic phase, i.e. the polysiloxanes, and which can easily be provided with terminal or lateral functional groups. The polymers comprised in the at least one hydrophilic block are preferably selected from a groups consisting of poly(vinyl alcohol), poly(ethylene glycol), poly(hydroxyethyl methacrylate), polyacrylamide, poly(N-vinyl-pyrrolidone), polyacrylic acid, poly(methacrylic acid), poly(maleic anhydride) and polymaleic acid, most preferably said polymers are poly(ethylene glycol).

According to yet a further embodiment, the at least one block of hydrophilic units has terminal or lateral functional groups. The most important characteristics of the functional groups are that they are water-stable and that they easily react with nucleophilic groups such as amino-groups and thiol-groups. Thus, said functional groups are selected from the groups consisting of isocyanates, isothiocyanates, acrylates, maleinates, N-hydroxysuccinimide esters and cyanoacrylates, preferably the functional groups are isothiocyanates. Thus, according to the most preferred embodiment the at least one hydrophilic block is formed from compounds of the following structure:

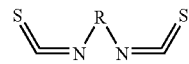

in which $R=(CH_2-CH_2-O)_a$ and a is 1-100,000, preferably 4-100.

According to one of the embodiment, the inventive amphiphilic block has the following formula:

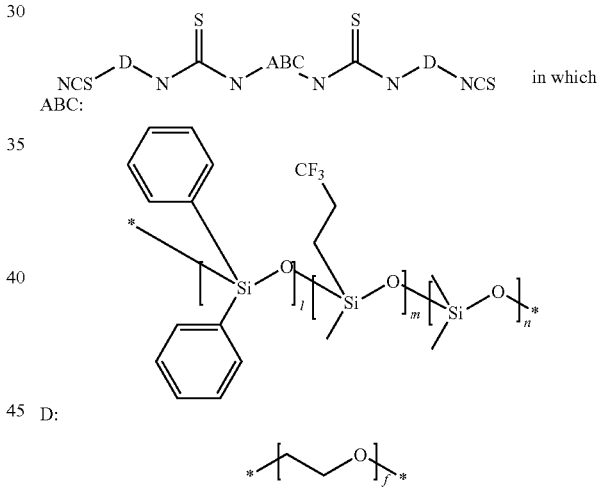

and l is from 1-10, m is from 1-20, n is from 1-100 and f is from 1-40.

The amphiphilic block copolymers according to the present invention can also have structures alternative to the tri-block copolymers as shown above, such as di-block, multi-block graft block and star block. A preferred structure is the tri-block.

Another aspect of the present invention is to provide a composition comprising amphiphilic block copolymers wherein the at least one hydrophobic block comprises terminal or lateral functional groups capable of reacting with the nucleophilic groups on the tissue surface and at least one hydrophobic block comprises hydrophobic polymers capable of interacting with an implant whereby a connection is obtained between the implant and the tissue surface. Preferably the polymers in the hydrophobic block of the amphiphilic block copolymer comprise essentially the same polymers as the implant since this will provide the best hydrophobic interaction. According to one embodiment of the present invention the composition comprises the amphiphilic copolymers disclosed above. The compositions are preferably ophthalmic compositions since they are intended for applications in the eye, it is therefore very important that the compositions do not interrupt the light pathway through the eye. It is also preferred that the compositions are aqueous or at least comprise a biocompatible solvent since they will be used for modifying a tissue surface by forming a coating on said surface, i.e. they will be used for applications in the body. Preferably the compositions are aqueous emulsions.

The use of the inventive compositions is provided by another aspect of the present invention, especially for applications regarding coating a tissue surface with said compositions, preventing and/or reducing secondary cataract and providing a connection between a hydrophilic tissue and a hydrophobic implant. However, persons skilled in the art can find other applications for the present invention. The inventive composition is injected in close connection to the tissue surface to be coated, preferably the tissue surface is located in a closed cavity. The functional groups of the amphiphilic block copolymers will react with the nucleophilic groups, such as the amino-groups, of the body tissue, thus forming a coating on the tissue. When a hydrophobic implant is placed in association with a tissue coated with the amphiphilic block copolymers according to the present invention, the at least one hydrophobic block of said copolymer will interact with the implant, thus forming a connection (i.e. "a bridge") between the tissue surface and the implant thereby ensuring that the implant is secured to the tissue.

Compositions according to the invention have a general usefulness for injection into cavities of the body, either naturally occurring or surgically construed for linking implants to body tissues, for example to improve compliance or ensure the correct, intended function of the implant. For example, compositions of the presently invented amphiphilic copolymers will, when applied to the contact region between tissue and implant in conjunction with the surgical process, increase safety and compliance of breast implants or other implants in cosmetic surgery. In ophthalmic applications, for example in cataract surgery, compositions according to the present invention may be applied to an intraocular lens as a coating (for example, on the lenses posterior side). The coated lens may then be inserted into the capsular bag as in typical cataract surgery, with the posterior side of the lens in contact with the posterior side of the capsular bag so that the amphiphilic copolymer will adhere to the lens and to the capsular bag (i.e. bridging the lens-bag interface) and thereby reduce posterior capsular opacification. Also the position of the lens in the capsular bag can be secured by adhering the lens to the capsular bag. For instance when the lens is an asymmetric lens (e.g., a toric lens that corrects for astigmatism of the cornea), it is important that the lens is fixated in a pre-determined position.

According to a specific embodiment, the inventive composition can be injected into the capsular bag of the eye by the use of a conventional cannula. In the capsular bag the functional groups of the amphiphilic block copolymer will react with the nucleophilic groups, such as amino-groups or thiol-groups, of the interior surface of the capsular bag. After a certain appropriate time, the excess of the composition is removed and the artificial lens is either injected or implanted. According to the present invention, an intraocular lens is injected as an ophthalmic composition, said composition preferably comprises the same siloxane terpolymers as the siloxane terpolymers of the amphiphilic block copolymer, which is then cured by using the capsular bag as a mold. The at least one hydrophobic block of said amphiphilic block copolymers will interact with the hydrophobic lens thus creating a close connection between the capsular bag and the lens. This close connection prevents and/or reduces the growing of epithelial cells since there is no space for them to grow (due to the close connection and due to the fact that the wall of the capsular bag is covered with a coating). The advantage of using the inventive composition invention is that the amphiphilic block copolymers will improve the adhesion between the capsular bag and the intraocular lens, which may improve the accommodation of the lens and capsular bag. Zonules attached to the capsular bag distort the bag during accommodation, and the attachment of the lens to the bag using embodiments of the present invention may allow the distorting forces of the zonules and bag to be more effectively applied and transmitted to the intraocular lens. Thus, one aspect of the present invention relates to the use of a composition comprising amphiphilic block copolymers for preventing and/or reducing secondary cataract and to a method for preventing and/or reducing secondary cataract by: removal of the natural lens; injection of the inventive composition into the eye, and specifically into the capsular bag; and insertion or injection of an intraocular lens, for example injection of an injectable intraocular lens.

Further aspects of the present invention relate to a joined structure and the use thereof. Said structure comprises a tissue surface, amphiphilic copolymers wherein the at least one hydrophilic block comprises terminal or lateral functional groups capable of reacting with the nucleophilic groups on the tissue surface and the at least one hydrophobic block comprises hydrophobic polymers capable of interacting with an implant whereby a layered structure is obtained comprising a tissue surface, an amphiphilic copolymer and an implant. According to one embodiment the amphiphilic copolymer is the amphiphilic copolymer disclosed above and therefore it is referred to the previous discussion regarding preferred polymers structures and functional groups. The structure is used in applications in the body such as creating a connection between an implant and a tissue surface and preventing secondary cataract, i.e. capsular opacification.

EXAMPLES

The following examples are included in order to illustrate the principles of the present invention and should not in anyway be interpreted as limiting to the scope of invention.

Example 1

Purification of $H_2N$-PEG-$NH_2$ 10.93 g aminopropyl-ended PEG (Aldrich) and a magnetic bar were added to a 50 ml beaker, and the sample was dissolved with $CHCl_3$ (12.1 g) to a total volume of ca 20 ml. A heating gun was used to melt PEG and also for increasing the dissolution. The obtained aminopropyl-ended PEG solution was clear and yellow and was then precipitated in ca 300 ml $Et_2O$ in room temperature (RT), i.e. the obtained solution was added to $Et_2O$ by a dripping funnel. This solution was cooled (in −18° C.) and then filtrated though a P4 glass filter and washed several times with $Et_2O$ and then dried in a beaker under vacuum (air pump) in RT. The obtained sample was transferred into an one-neck flask and dried with an oil pump for 2 h in RT and then freeze dehydrated over night and transferred into a 50 ml sample bottle under Argon. The sample color was changed from pale yellow wax to almost white powder. The sample was characterized with $^1HNMR$.

Example 2

Synthesis of a Polysiloxane having Terminal Amino-groups ($H_2N$—SP3-$NH_2$)

Octamethylcyclotetrasiloxane ($D_4$) and (3,3,3-trifluoropropyl)methylcyclo-trisiloxane ($F_3$) were distilled before use. Octaphenylcyclotetrasiloxane ($D_4''$) was recrystallized from toluene.

$D_4$ (67.65 g, 0.2281 mole), $D_4''$ (12.92 g, 0.0163 mole), $F_3$ (16.96 g, 0.0362 mole), 1,3-bis(3-aminopropyl)tetramethyldisiloxane (3.84 g, 0.0155 mole) and potassium silanolate (0.0991 g) were added to an oven-dried 100 ml thee-neck round-bottom flask equipped with an over-head stirrer. The mixture was purged with nitrogen though the top of the condenser for several minutes (2-3 bubbles per second) and was kept cold with cooling water. The mixture was then heated gradually from 23 to 110° C. (heater scale at 150° C.) during 1.5 h. The temperature was kept at 110° C. for ca 30 min and was then raised to 120° C. within 30 min (heater scale at 175° C.). The oil temperature was controlled with a digital thermocouple. The total time of heating at 120° C. was ca 162 h. Samples were taken out with a syringe in certain time interval curing the reaction (ca 0.5 ml each time) for GPC-testing. The obtained mixture (99.82 g) was cooled to 25° C. The obtained clear, colorless and viscous silicone oil was dissolved with 70 ml dichloromethane and poured into a 250 ml separation funnel and was then extracted with deionized water (70 ml×4 times). The phase-separation was fast (pH of the top layer ca 10) and the obtained product was washed twice with 70 ml methanol. The phase separation was fast (pH of the top methanol layer was 9-10). If the viscosity of the mixture was too high and the mixture was misty, "whitish", the mixture was diluted with a small amount of THF in order to reduce the viscosity and improve the extraction of low molecular weight components during washing. The mixture was diluted with 15 ml THF and washed once more with 70 ml methanol. The separation time was longer than the separation time for the water washing and it was also more difficult to see a clear board-line between the two layers. After the second time of washing with methanol, the mixture was allowed to have a longer separation time, which allowed as much methanol as possible to be separated from the polymer. The pH of the top layer was 8-9. The mixture became misty since there was too much methanol remaining in the polymer, therefore, ca 7 ml THF was added to form a clear and colorless solution and the mixture was washed with 70 ml of methanol again. pH of the top layer was ca 8. The solvent and volatiles were first removed with water pump, and then with an air pump (50° C. for 30 min) and an oil pump (<0.22 torr) in RT for 8 h. The obtained oil was clear and colorless, 69.20 g, and the yield 68.3%. The sample was characterized with GPC and NMR. Mn 11065, Mw 18188, Mp 16164, Mw/Mn 1.654.

Example 3

Synthesis of α, ω-bis-carboethoxy-dithiocarbamate Terminated poly(ethylene glycol) (EtOOCSSCNH$(CH_2)_3O(CH_2CH_2O)_n(CH_2)_3$NHCSSCOOEt or I) in Aqueous Media 4.42 g (2.71 mmol) of purified bis(3-aminopropyl) terminated poly(ethylene glycol) ($H_2N(CH_2)_3(OCH_2CH_2)nO(CH_2)_3NH_2$, Aldrich), 10 ml of water and a magnetic stirring bar were added to a 100 ml thee-neck round bottom flask. $H_2N(CH_2)_3(OCH_2CH_2)_nO(CH_2)_3NH_2$ was dissolved slowly in water in room temperature, which gave an opaque solution, and 5 ml MeOH was added. The solution became clear and palely yellow. The solution was cooled to −1 to −6° C. with ice-NaCl. 0.60 ml (9.95 mmol) of $CS_2$ was added drop by drop with a syringe and the solution was stirred and chilled. Ca 3 ml KOH solution containing 0.60 g KOH (10.69 mmol) was chilled to 0° C. and added though a dripping funnel. After $CS_2$ had reacted completely (ca 22 hours), the mixture was cooled to −3° C. with ice-NaCl and 1.00 ml (10.46 mmol) of ethyl chloroformate was added drop by drop with a syringe during 5 min The dark-yellow and clear solution became pale-yellow to yellow slurry and the ice-NaCl bath was removed 10 min later. The solution was reacted for one more hour and was then allowed to stand for an hour in RT. When the temperature rose, the slurry became dark yellow and the viscosity decreased. The obtained yellow and opaque solution was extracted with 30 ml ethyl ether for thee times until the top layer was colorless. The separation was fast. The top layer was green (pH 5-6), and the lower layer was yellow (pH 2), both layers were clear. Some of solvent was evaporated and the solution was precipitated in more than 10 times of ether and the ether was decanted. Yellow oil was obtained and dried under vacuum (air pump) in RT over night. The sample was still oil with slurry, yellow, and then dried with an oil pump in RT, 0.46-0.5 torr for ca 5.5 h. 3.59 g of a yellow wax was obtained, which is I, yield 93%.

Example 4

Synthesis of bisisothiocyanate-terminated poly(ethylene glycol) (II or SCN-PEG-NCS) in Aqueous Media 3.59 g (1.87 mmol) I was dissolved with 10 ml dried $CHCl_3$, and stirred with a magnetic bar until the dissolution was completed (yellow opaque). 1.00 ml $Et_3N$ (7.14 mmol) was added slowly drop by drop with a syringe and the solution was reacted for ca 1.5 h in RT. After 30 min of reaction, additional 4.1 ml $Et_3N$ (29.27 mmol) was added. The solvent was stripped with a water pump at RT overnight. The pale-yellow powder sample was dried with oil pump (0.4 torr) in RT for another 7 h, and then freeze dehydrated overnight (0.055 mbar, −53° C.). 3.37 g of pale brown powder was obtained as crude product. 5 ml $CHCl_3$ was added drop by drop to 3.28 g of the crude product to obtain ca 10 ml (total volume) of viscous, dark yellow solution. The solution was precipitated in ca 150 ml $Et_2O$ in RT and was then cooled in a refrigerator for 1.5 h. The solution was then filtrated though a P4 glass filter and the precipitate was washed for several times with $Et_2O$ and dried in RT under vacuum (air pump) overnight, and then freeze dehydrated under vacuum (−52° C., 0.064-0.058 mbar) overnight. 2.69 g of an almost white powder was obtained and the yield was 86%.

Example 5

Synthesis of bisisothiocyanate-terminated poly(dimethyl-co-diphenyl-co-triflouropropylmethylsiloxane)-b-poly(ethylene glycol) (III or SCN-PEG-b-SP3-b-PEG-NCS)

Example 5a 1.09 g (0.64 mmol) II, a magnetic bar and 2 ml of chloroform were added to a 100 ml one-neck flask. When II was completely dissolved into a yellow and opaque solution, 0.01 g (one drop) Sn(oct)$_2$ (FW 405.1) as catalyst was added directly. Then 3.83 g (0.32 mmol) of bisamino-terminated poly(dimethyl-co-diphenyl-co-triflouropropylmethylsiloxane) ($H_2N$—SP3-$NH_2$) in 14 ml chloroform was added slowly drop by drop via a side-arm dripping funnel during 3 h in RT. When the dripping was finished, the temperature was raised to 45° C. and kept over the weekend. The solution was cooled to RT. Some of solvent was evaporated with a water pump to keep oil:$CHCl_3$=60:42. The yellow and viscous solution was then transferred to a separating funnel with ca 5 ml chloroform. The content of the funnel was shaken for a short while and thus mixed. The diluted mixture was then washed, first with ca 5 ml water. Separation was difficult and slow (2 h). No separation at all. The emulsion was almost white and ca 5 ml MeOH was added to improve separation, which seems to be effective. The top layer was white, opaque, pH 5-6; the bottom layer was yellow, opaque, viscous, and the volume was increased. The solution was washed with ca 10 ml of water again and separation was faster than the first time (during the second washing the pH of top layer was 6). Chloroform was added to dilute the solution, which was too viscous. The lower layer was pale yellow. pH of top layer was 5-6 for third washing and separation was difficult to achieve. The obtained emulsion was almost white and was kept overnight. After separation, the solution was stripped with water pump for 2.5 h. Most of solvent was removed on rotary evaporator at 50° C. The product became white soft solid with very strong emulsifying ability and easily soluble in THF. The product was dried in RT with air pump overnight, and then with oil pump (0.16 torr) for 30 min, and followed by freeze dehydrated overnight. 4.0151 g yellow and soft solid was obtained in a yield of 82%.

Example 5b

The used amino-ended SP3 has the following molecular weight:

| $H_2N$-$SP_3$-$NH_2$ | Mn | Mw | Mw/Mn | Note |
|---|---|---|---|---|
| I | 11065 | 16164 | 1.654 | 162 h, purified |

The calculation was based on $H_2N$—SP3-$NH_2$ (I) FW as 11065, $SCN(CH_2)_3O(CH_2CH_2O)_n(CH_2)_3NCS$ (II) FW as 1712, and molar ratio I:II=1:2, 0.68 g (0.40 mmol) II, a magnetic bar and 2 ml of anhydrous chloroform were added to a 100 ml one-neck flask. When II was completely dissolved to an orange, clear solution, 2.7 mg (one drop) of Sn(oct)$_2$ (FW 405.1) as catalyst was added directly. Then 2.21 g (0.20 mmol) I in ca13 ml of anhydrous chloroform was added slowly drop by drop via a side-arm dripping funnel during 1.25 h at RT. When the dripping was finished the obtained solution was orange and clear. The temperature was raised to 45° C. with an oil bath and kept for ca 42 h. The solution was orange but lighter than before, clear and had very low viscosity and was cooled to RT and precipitated in ca 300 ml of Et$_2$O in RT to remove un-reacted PEG. No precipitate appeared. The ether solution was pale yellow, opaque with fluorescing and was filtrated though a P4 sintered glass filter. After the filtration, the solution was still opaque with fluorescing. The solvent was evaporated on a rotary evaporator. 2.74 g of wet sample was transferred to a 25 ml one-neck flask with 20 ml of $CH_2Cl_2$. The solvent was evaporated on rotary evaporator again, and then the sample was dried with air pump over the weekend, and then freeze dehydrated overnight. The obtained sample was dark yellow gel, 2.53 g, and was characterized with GPC and NMR.

The washing procedure of dichloromethane solution with water and methanol was omitted.

Example 5c

The used amino-ended SP3 has the following molecular weight:

| $H_2N$-$SP_3$-$NH_2$ | Mn | Mw | Mw/Mn | Note |
|---|---|---|---|---|
| I | 11065 | 16164 | 1.654 | 162 h, purified |

The calculation was based on $H_2N$—SP3-$NH_2$ (I) FW as 11065, $SCN(CH_2)_3O(CH_2CH_2O)_n(CH_2)_3NCS$ (II) FW as 1712, and molar ratio I:II=2:1, 0.17 g (0.10 mmol) II and a magnetic bar and 2 ml (ca 2.85 g) of anhydrous chloroform were added to a 100 ml one-neck flask. When II was dissolved completely to an orange and clear solution, 6.2 mg (two drops) of Sn(oct)$_2$ (FW 405.1) as catalyst was added directly. Then 2.21 g (0.20 mmol) I in ca13 ml of anhydrous chloroform was added slowly drop by drop by using a dripping funnel during 1.47 h at RT. When the dripping was finished, the obtained solution was light yellow and clear. The temperature was increased to 45° C. with an oil bath and kept for ca40 h. The solution was light yellow, clear and had very low viscosity and was cooled to RT and precipitated in ca 300 ml of Et$_2$O in RT to remove un-reacted PEG. No precipitate appeared. The solution was colorless and clear without fluorescing and was filtrated though a P4 sintered glass filter. After filtration, the obtained solution was colorless and clear. The solvent was evaporated on the rotary evaporator. 2.90 g yellow oil was transferred into a 10 ml one-neck flask with several milliliters of anhydrous chloroform. The solvent was evaporated with water pump over the weekend, and then air pump and oil pump. The obtained sample was viscous, yellow oil, 2.18 g, characterized with GPC and NMR.

Example 5d

The used amino-ended SP3 has the following molecular weight:

| $H_2N$-$SP_3$-$NH_2$ | Mn | Mw | Mw/Mn | Note |
|---|---|---|---|---|
| I | 11065 | 16164 | 1.654 | 162 h, purified |

The calculation was based on $H_2N$—SP3-$NH_2$ (I) FW as 11065, $SCN(CH_2)_3O(CH_2CH_2O)_n(CH_2)_3NCS$ (II) FW as 1712, and molar ratio I:II=1:1, 0.34 g (0.20 mmol) II, a magnetic bar and 2 ml (ca 2.85 g) of anhydrous chloroform were added to a 100 ml one-neck flask. When II was completely dissolved to an orange, clear solution, 4.5 mg (two drops) of Sn(oct)$_2$ (FW 405.1) as catalyst was directly added. Then, 2.21 g (0.20 mmol) I in ca13 ml of anhydrous chloroform was added slowly drop by drop with a side-arm dripping funnel during 1.23 h in RT. When the dripping was finished, the obtained solution was light yellow and clear. The temperature was increased to 45° C. with an oil bath and kept for ca 42 h. The solution was light yellow, clear and had very low viscosity and was cooled to RT and precipitated in ca 300 ml of Et$_2$O in RT to remove un-reacted PEG. No precipitate appeared. The solution was trace yellow, opaque with fluorescing and was filtrated though a P4 sintered glass filter. After filtration, the solution is trace yellow and opaque. The solvent was evaporated on the rotary evaporator. The yellow, viscous oil was transferred into a 10 ml one-neck flask with several milliliters of anhydrous chloroform. The solvent was evaporated with water pump over night and then oil pump (0.21 torr). Orange, highly viscous oil was obtained, 2.42 g.

Results from the Characterization of the Copolymers
a) GPC

| Samples | Retention time | Mw | Mv | SP3:PEG |
|---|---|---|---|---|
| SP3-b-PEG-11 | 24.390 | 612477 | 154629 | 1:1 |
| SP3-b-PEG-21 | 24.574 | 202076 | 70038 | 2:1 |
| SP3-b-PEG-12avg* | 23,330 | 1000515 | 390329 | 1:2 |
| SP3 | | 25.073 | 49297 | 40989 |
| $H_2$N-PEG-N$H_2$ | 27.576 | 2100 | 1950 | |

*Different test of sample set bis-$H_2$N-SP3 (I) FW = 11065 and SCN($CH_2$)$_3$O($CH_2CH_2$O)$_n$($CH_2$)$_3$NCS (II) FW = 1712

Figure 1B:
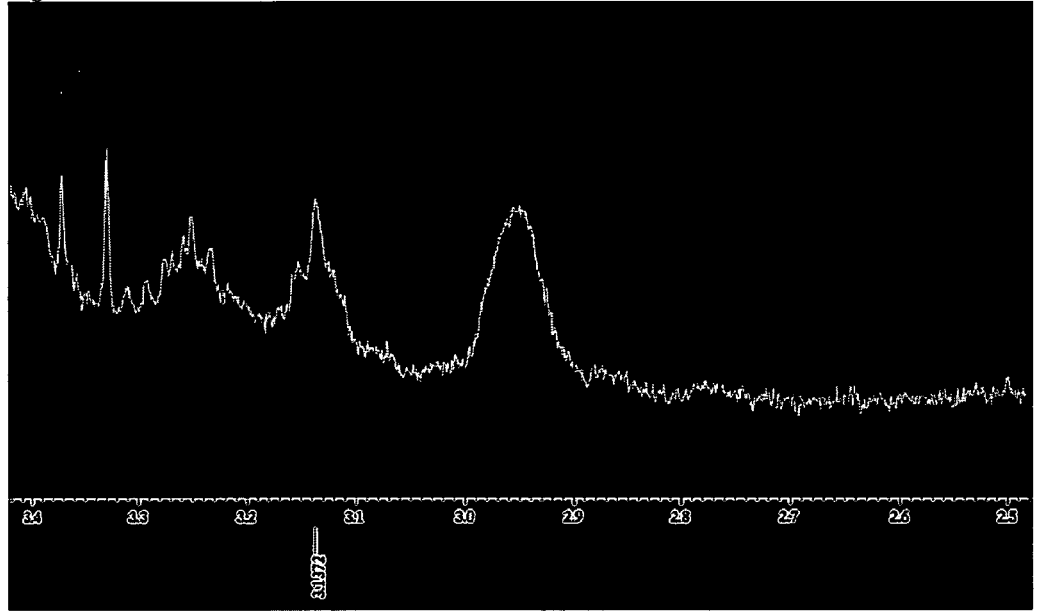

The most change in molecular weight can be indicated by Mw and Mv, which changes with the molar ratio of polysiloxane segment and PEG segment.

b) NMR (see FIGS. 1A and 1B)

$^1$H-NMR of $H_2$N-ended PEG has chemical shifts at 2.57-2.87 ppm, which are methylene protons connecting amino groups. They disappeared on the spectrum of $^1$H-NMR of SCN-ended PEG and a chemical shift appeared at 3.06-3.12 ppm, which is methylene protons connecting NCS groups. After the copolymerization of SCN-PEG-NCS and H2N—SP3-NH2, molar ratio 2:1, there is a chemical shift at 3.14 ppm. It should be methylene protons connecting the NCS groups.

Example 6

Interaction Between the Copolymer and the Model Protein Surface

The model protein surface is a commercial collagen film. Two different processes were used for coating the copolymer onto the collagen films.

Example 6a

A piece of collagen film (ca 5×7 mm) and deionized water was added to a 4 ml vial. The collagen film swelled fast and formed an opaque large film and then the pH was adjusted to ca 9 with 0.1 M NaOH. The solution was mixed with an electric rotary mixer.

0.0909 g of the PEG-b-SP3 block copolymer and water (0.6722 g) was added to another 4 ml vial. The polymer was not soluble and seemed not to swell even though a rotary mixer was used (vigorously stirring). 0.4242 g of $CHCl_3$ was then added and the polymer swelled immediately. When the rotary mixer was used, a white emulsion was formed fast. Its pH was adjusted to above 9 with 0.1 M NaOH.

The swelled film was transferred into the emulsion solution of the copolymer and mixed with the rotary mixer in RT overnight. The emulsion was uniform and white. But next morning, some separation was found.

Figure 3A:
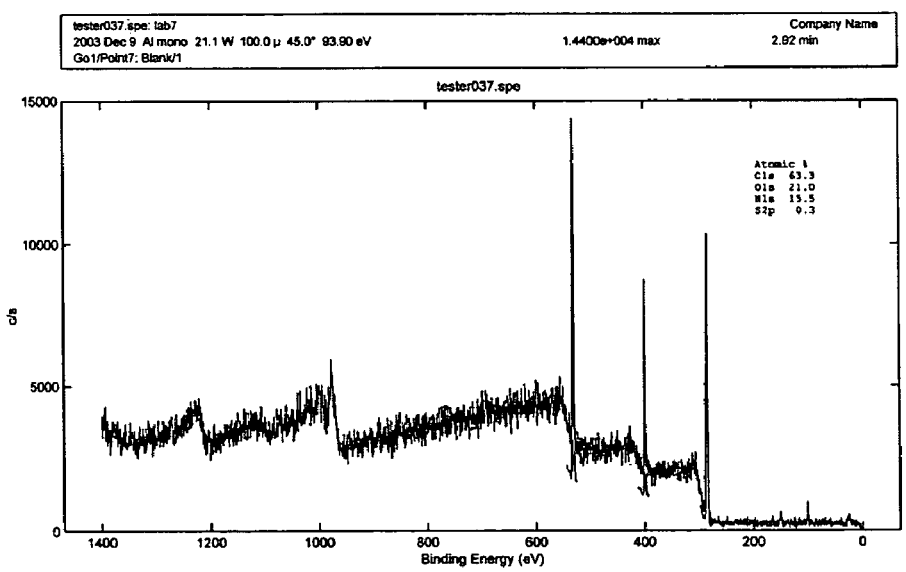
FIGS. 3A and 3B set forth ESCA spectra of an interaction between a copolymer according to a further embodiment and a collagen film.

The obtained product was extracted with THF in a Soxhlet extractor over the weekend and then dried in a vacuum oven for several days in room temperature. The film was white and opaque after drying. Before the measurement, the film was placed in a high vacuum chamber ($1\times10^{-9}$ mbar) on the scanning ESCA instrument to removal trace amount of low molecular weight contaminants. Two different positions were detected. The calculation was based on their average values (see FIG. 3A).

Example 6b 0.0716 g of the PEG-b-SP3 block copolymer and $CHCl_3$ (0.5700 g) was added to a 4 ml vial. The polymer swelled fast and was soluble with a rotary mixer. 0.7671 g of water was added. A white emulsion was formed without the use of NaOH after stirring and pH was 7-8.

A piece of collagen film (0.0064 g) and deionized water was added (pH<7) to another 4 ml vial, which swelled fast to form an opaque large film and then the pH was adjusted to ca 9 with 0.1 M NaOH. The solution was mixed with an electric rotary mixer. The swelled film was transferred into the emulsion solution and mixed with the rotary mixer in RT overnight. The emulsion was uniform and white. Next morning, the emulsion was stirred and heated at 40° C. with water bath for 5.5 h.

Figure 3B:
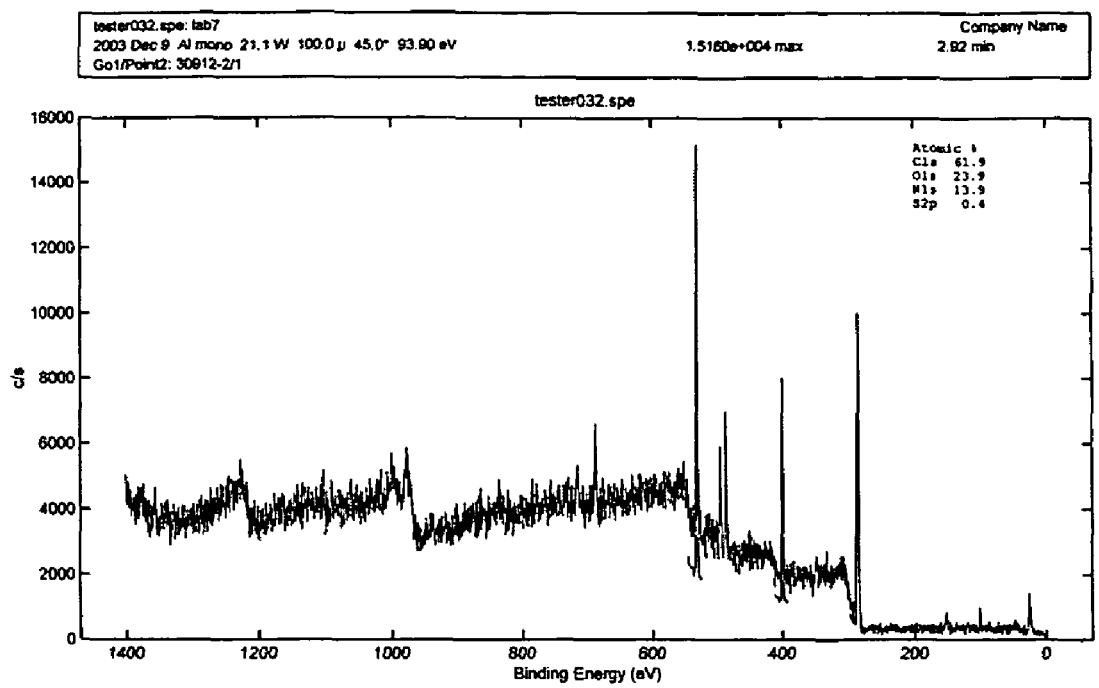

The obtained product was extracted with THF in a Soxhlet extractor over the weekend and then dried in a vacuum oven for several days in room temperature. The film was white and opaque after drying. Before the measurement, the film was placed in a high vacuum chamber ($1\times10^{-9}$ mbar) on the scanning ESCA instrument to removal trace amount of low molecular weight contaminants. Two different positions were detected. The calculation was based on their average values (see FIG. 3B).

Results from Example 6

Figure 2:
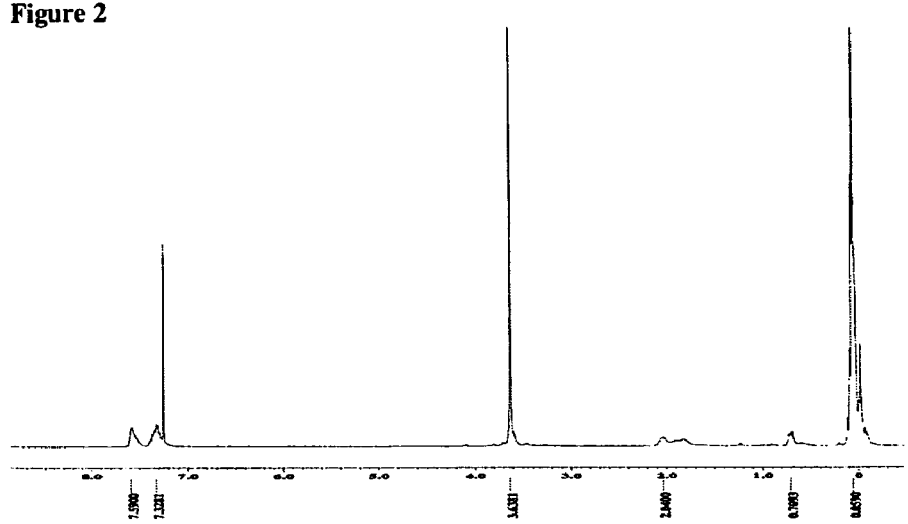
FIG. 2 sets forth a $^1$H-MNR spectra of an interaction between a copolymer according to an embodiment of the present invention and a model protein surface.

Structural Characterization with $^1$H-NMR $^1$H-NMR was used for estimating the composition of the copolymer. For example, the copolymer has a feeding molar ratio of NCS-ended PEG to amino-ended polysiloxane at 1:1. FIG. 2 is its $^1$H-NMR spectrum. In Table 1, a, b, c and d represent the average unit numbers of $D_4$", $F_3$, $D_4$, and PEG respectively. Based on the integration intensity ratio at 7.33-7.6 ppm and 3.64, and if we assume the average repeat unit number of PEG d=34, the same value as one from the Aldrich product, thus, a=6.8. For b and c, in fact, the specific peak intensities should be used for calculating the actual repeat unit number, such as $CF_3$—$\underline{CH_2}$— at 1.9-2.0 ppm and C$\underline{H_3}$—Si— at ~0.1-0.3 ppm. But this is inconvenient. Therefore, we assume SP3 segment in the copolymer has the same structure as in amino-ended SP3 and a, b and c keep the same unit ratio as one in the feeding. Thus, b=11.3 and c=95.2.

TABLE 1

| Repeat Units | $(Ph_2SiO)_a$ | $(CF_3CH_2CH_2MeSiO)_b$ | $(Me_2SiO)_c$ | $(CH_2CH_2O)_d$ |
|---|---|---|---|---|
| Number codes | a | b | c | d |
| Numbers | 6.8 | 11.3 | 95.2 | 34 |

$^1$H-NMR also shows the methylene protons neighbouring to NCS in both NCS-ended PEG and NCS-ended copolymer.

Evidence for the Attachment of NCS-functionalized Amphiphilic Block Copolymer Based on Polysiloxane and Poly(Ethylene Glycol) (PEG-b-SP3) onto the Collagen Film:

Comparing the blank sample (FIG. 3A) with the copolymer-coated collagen film ((FIG. 3B), coated with method Ex. 6B), there is a peak at 680 eV on the block copolymer, which is characteristic of the fluorine 1s electron. The fluorine comes from the $F_3$ unit of polysiloxane segment, and the polysiloxane segment belongs to the copolymer. Therefore, ESCA confirms the attachment of the copolymer onto the surface of collagen film.

In addition, by comparing the relative atomic concentration of C, N and O (Table 1), we can see that both O and C concentrations increase in NCS-ended PEG coated collagen and NCS-ended copolymer coated collagen. It implies that the coating with both of them on the collagen surface was obtained.

TABLE 2

ESCA Data

| | Relative Atomic Concentration | | |
|---|---|---|---|
| | N1s | O1s | C1s |
| Blank collagen film | 1,000 | 1,355 | 4,084 |
| NCS-ended PEG | 1,000 | 1,706 | 6,413 |
| NCS-ended PEG-b-SP3 | 1,000 | 1,719 | 4,453 |

Compared with reference film, which was not coated, the concentrations (c/s) of sulfur 2p electrons are different among the coated samples (Table 3). All of the coated samples have higher sulfur concentration than the reference. This can be explained with the reaction of NCS to the nucleophilic functional groups on the collagen surface.

TABLE 3

ESCA Data for $S_{2p}$

| | c/s | Binding Energy, eV |
|---|---|---|
| Blank collagen film | 196 | 167.0-167.8 |
| NCS-ended PEG-b-SP3, No. I | 318 | 161.0-161.6 |
| NCS-ended PEG-b-SP3, No. II | 270 | 160.5-161.0 |
| NCS-ended PEG | 395 | 167.2-167.8 |
| Phenyl NCS | 375 | 168.5-167.8 |
| FITC | 270 | 167.0-167.8-168.5 |
| Ethyl NCS | 279 | 167.3-167.5-168.5 |

Example 7

Interaction Between Copolymer, Implant and Tissue in a Pig's Eye (Synthesis of SCN-PEG-NCS-b-$H_2N$—SP3-$NH_2$)

The amino-ended SP3 (polysiloxane copolymer) has molecular weight Mn 12044, PD 1.80 by SEC, which was coded as (I), and $SCN(CH_2)_3O(CH_2CH_2O)_n(CH_2)_3NCS$ coded as (II) has molecular weight 1712 (n=34), keeping molar ratio I:II=1:2. To a 100 ml one-neck flask, 1.09 g (0.64 mmol) II, a magnetic bar and 2 ml chloroform were added. When II was dissolved completely, ca. 0.01 g $Sn(oct)_2$ (FW 405.1) as catalyst was added directly. And then, 3.83 g (0.32 mmol) I in 14 ml chloroform was added dropwise slowly via a side-arm dropping funnel during 3 hours at Room Temperature. When dropping was finished, the temperature was increased to 45° C., for ca. 66 hrs. The product was purified with the standard method for SP3, yield 82%, which was a light yellow soft solid. The solid copolymer was dispersed with ethanol and diluted with water to an emulsion E with final concentration of polymer 11.5% and ethanol 65.5%.

The natural lens inside the intact capsular bag was taken out of a fresh ennucleated pig's eye from the slaughter house by an ophthalmic surgeon. With forceps the capsular bag was grabbed and pulled outwards for a distance of a few mm. The natural lens material adhered to the capsular bag. This was demonstrated because the lens material followed the outward movement of the capsular bag.

In another fresh pig's eye, the natural lens was removed (by sucking through a large injection needle) from the capsular bag through a small capsular rhexis of about 1.5 mm diameter. Then the capsular bag was filled with emulsion E. After 5 minutes the emulsion was removed by rinsing with balanced salt solution (BSS), and subsequently the capsular bag was filled with a silicon pre-polymer mixture that polymerized in the capsular bag within 60 minutes forming a flexible silicone gel with a modulus ≦2 kPa imitating an artificial human crystalline lens. By pulling the capsular bag with a forceps, the artificial lens content followed the outward movement of the capsular bag demonstrating that there has been formed a bond between the capsular bag and the artificial lens material.

The test was repeated with a fresh pig's eye, but this time no capsular treatment was given after the removal of the natural lens and before refilling with the artificial lens forming silicone polymer. By pulling the capsular bag with forceps; only the capsular bag followed the outward movement. The artificial lens content did not move. This demonstrated the absence of a bond between artificial lens and the capsular bag in the case of an untreated capsular bag.

The specific embodiments and examples described herein are illustrious in nature only and are not intended to be limiting of the invention defined by the claims. Additional embodiments and examples of the various aspects of the invention defined by the claims and/or which are equivalent to the specific embodiments and examples set forth herein may be apparent to one of ordinary skill in the art and are included within the scope of the claimed invention.

The invention claimed is:

1. A coating composition for adhering an implant to a biological tissue comprising an amphiphilic block copolymer having at least one block of hydrophilic units and at least one block of hydrophobic units wherein said at least one hydrophobic block contains siloxane units, the siloxane units having the formula:

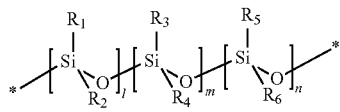

wherein said hydrophobic block is a terpolymer in which $R_1$, $R_2$ and $R_6$ are methyl, $R_3$ and $R_4$ are phenyl and $R_5$ is trifluoropropyl.

2. A coating composition for adhering an implant to a biological tissue comprising an amphiphilic block copolymer having at least one block of hydrophilic units and at least one block of hydrophobic units wherein said at least one hydrophobic block contains siloxane units, the siloxane units having the formula:

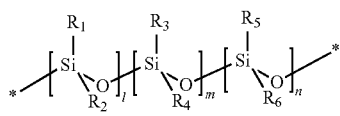

wherein said hydrophobic block is a terpolymer in which $R_1$, $R_2$ and $R_6$ are methyl, $R_3$ and $R_4$ are phenyl and $R_5$ is trifluoropropyl, wherein the terpolymers have terminal amino groups.

3. The composition according to claim 1, wherein said at least one block of hydrophilic units comprises a polymer selected from the group consisting of poly(vinyl alcohol), poly(ethylene glycol), poly(hydroxyethyl methacrylate), polyacrylamide, poly(N-vinyl-pyrrolidone), polyacrylic acid, poly(methacrylic acid), poly(maleic anhydride) and polymaleic acid.

4. The composition according to claim 3, wherein said at least one block of hydrophilic units are poly(ethylene glycol).

5. The composition according to claim 1, wherein said at least one hydrophilic block comprises terminal or lateral functional groups.

6. The composition according to claim 5 wherein said terminal or lateral groups are selected from functional groups which are water stable and which capable of reacting with nucleophilic groups.

7. The composition according to claim 5, wherein said terminal or lateral functional groups are selected from the group consisting of isocyanates, isothiocyanates, acrylates, maleinates, N-hydroxysuccimide esters and cyanoacrylates.

8. The composition according to claim 7, wherein said terminally functional groups are selected from isothiocyanates.

9. The composition according to claim 1, wherein said at least one hydrophilic block is formed from a precursor with the structure

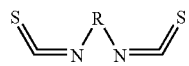

in which formula R is $(CH_2-CH_2-O)_a$ and a is 1-100 000.

10. A coating composition for adhering an implant to a biological tissue comprising an amphiphilic block copolymer comprising an amphiphilic block copolymer comprising at least one block of hydrophilic units and at least one block of hydrophobic units, wherein said at least one hydrophobic block contains siloxane units, and wherein said amphiphilic block copolymer is an isothiocyanate terminated poly(ethylene glycol)-b-polysiloxane having the formula:

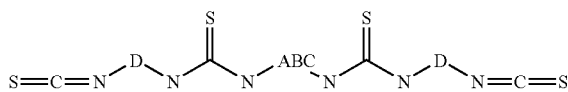

in which
ABC:

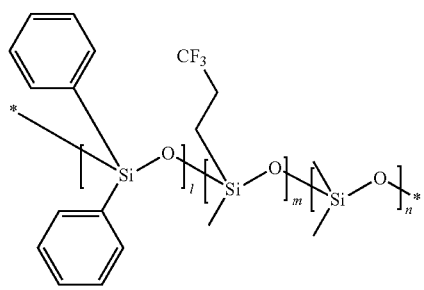

D:

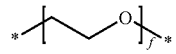

and l is from 1-10, b is from 1-20 and c is from 1-100 and f is from 1-40.

11. The composition according to claim 1 wherein said composition is an ophthalmic composition.

12. The composition according to claim 1 wherein said composition is an aqueous emulsion.

13. The composition according to claim 2 wherein said terminal or lateral groups are selected from functional groups which are water stable and which capable of reacting with amino-groups.

14. The composition according to claim 2 wherein said at least one block of hydrophilic units comprises a polymer selected from the group consisting of poly(vinyl alcohol), poly(ethylene glycol), poly(hydroxyethyl methacrylate), polyacrylamide, poly(N-vinyl-pyrrolidone), polyacrylic acid, poly(methacrylic acid), poly(maleic anhydride) and polymaleic acid.

15. The composition according to claim 14, wherein said at least one block of hydrophilic units are poly(ethylene glycol).

16. The composition according to claim 2, wherein said at least one hydrophilic block comprises terminal or lateral functional groups.

17. The composition according to claim 16 wherein said terminal or lateral groups are selected from functional groups which are water stable and which capable of reacting with nucleophilic groups.

18. The composition according to claim 16, wherein said terminal or lateral functional groups are selected from the group consisting of isocyanates, isothiocyanates, acrylates, maleinates, N-hydroxysuccimide esters and cyanoacrylates.

19. The composition according to claim 18, wherein said terminally functional groups are selected from isothiocyanates.

20. The composition according to claim 2, wherein said at least one hydrophilic block is formed from a precursor with the structure

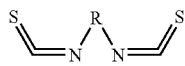

in which formula R is $(CH_2-CH_2-O)_a$ and a is 1-100 000.

* * * * *